| United States Patent [19] | [11] | 4,208,479 |
|---|---|---|
| Zuk et al. | [45] | Jun. 17, 1980 |

[54] LABEL MODIFIED IMMUNOASSAYS

[75] Inventors: Robert F. Zuk, Mountain View; Edward T. Maggio, Redwood City, both of Calif.

[73] Assignee: Syva Company, Palo Alto, Calif.

[21] Appl. No.: 815,632

[22] Filed: Jul. 14, 1977

[51] Int. Cl.² .................... G01N 31/14; G01N 21/22; G01N 33/16

[52] U.S. Cl. .................................. 435/7; 23/230 B; 424/8; 424/12

[58] Field of Search ................ 195/103.5 A, 103.5 R, 195/99, 127; 424/12, 8; 23/230 B

[56] References Cited

U.S. PATENT DOCUMENTS

| 3,996,345 | 12/1976 | Ullman et al. ........................ 428/8 X |
| 3,998,943 | 12/1976 | Ullman .................................. 428/8 X |
| 4,036,946 | 7/1977 | Kleinerman ............................. 424/8 |

OTHER PUBLICATIONS

Wei, et al., "Preparation of a Phospholipase C-Antihuman IgG Conjugate, and Inhibition of its Enzymatic Activity by Human IgG," *Clin. Chem.,* vol. 23, No. 8, (1977) pp. 1386-1388.

*Primary Examiner*—Thomas G. Wiseman
*Attorney, Agent, or Firm*—Bertram I. Rowland

[57] ABSTRACT

Methods and reagents are provided for immunoassays employing as reagents a labelled receptor, where the label is capable of providing a detectable signal, and modifying reagents, capable of modifying the signal obtained from the label. When ligand (ligand analog for monoepitopic ligands) is present in the assay medium, a complex is formed which inhibits interaction between the label modifying reagent and the label. By measuring the signal obtained in the presence of a known amount of ligand in the assay medium and comparing that signal with the signal obtained with an unknown sample suspected of containing ligand, one can qualitatively or quantitatively determine the amount of ligand in the unknown. For determinating anti(ligand) the assay is carried out in substantially the same way, except a source of ligand or ligand analog must be provided.

37 Claims, No Drawings

LABEL MODIFIED IMMUNOASSAYS

BACKGROUND OF THE INVENTION

1. Field of the Invention

There is an expanding interest in the ability to determine or monitor small amounts of organic antigenic or haptenic materials. Frequently, the concentrations of interest are micromolar or less. Various techniques have been developed which are capable of isolating and detecting a specific compound, despite the presence of myriad other compounds of similar and different structure.

One group of techniques referred to as competitive protein binding assays or immunoassays depend for their specificity on the use of a receptor, normally an antibody, which is specific for a compound of a particular spatial and polar organization. For these assays it is normally necessary to produce antibodies by injecting antigens or hapten conjugated antigens into a vertebrate to induce the formation of antibodies which may then be harvested. The bleeds which are obtained can be usually purified to separate a globulin concentrate from other proteinaceous materials. To further purify the globulin concentrate to separate the antibodies of interest from other globulins is only difficultly achieved.

While affinity chromatography will provide for some concentration of the desired antibodies, the procedure is normally slow and frequently results in substantial loss of the desired antibodies as well as reduction in the binding constant. That is, those antibodies in the composition which have the strongest binding, frequently cannot be removed from the column. Therefore, most methods have avoided labeling antibodies, since either the antibodies had to be purified to concentrate the antibodies of interest or a large amount of label was introduced associated with proteins which were not involved in the assay. This normally results in a large background signal which inevitably reduces the sensitivity of the assay, unless a physical separation of the extraneous label is incorporated into the procedure.

The alternative has been to label ligand. While labeling of ligand is feasible where the ligand is a simple hapten or the antigens are available in substantially pure form, in those situations where the antigen is only difficultly purifiable, exists in only small amounts, or is labile, labeling of antigens is not feasible for a commercial process.

An assay is therefore desirable which avoids the problems of purification and isolation of both the antibodies of interest and the ligand of interest. In addition, the assay should provide for minimizing introduction of label into the assay medium which produces a signal which interferes with or is additive with the signal which is measured.

2. Brief Description of the Prior Art

Radioimmunoassay is described in two articles by Murphy, J. Clin. Endocr. 27, 973 (1967); ibid 28, 343 (1968). U.S. Pat. No. 3,817,837 teaches a homogeneous enzyme immunoassay. U.S. Pat. Nos. 3,654,090, 3,791,932, 3,850,752 and 3,839,153 teach heterogeneous enzyme immunoassays. In the agenda for the Ninth Annual Symposium on Advanced Analytical Concepts for the Clinical Laboratory, to be held March 17 and 18, 1977 at the Oakridge National Laboratory, a paper entitled "Phospholipase C-Labeled Antihuman IgG: Inhibition of Enzyme Activity by human IgG," to be presented by R. Wei and S. Riebe is reported. U.S. Pat. Nos. 3,935,074 and 3,998,943 disclose immunoassay techniques involving steric inhibition between two different receptors for different epitopic sites. U.S. Pat. No. 3,996,345 teaches the use of a common receptor, a portion of which is bound to a fluorescer and the remaining portion bound to quencher, whereby the presence of ligand brings the receptors together so as to allow for quenching of fluorescence. Carrico, et al, Anal. Biochem. 72 271 (1976) and Schroder, et al, ibid 72 283 (1976) teach competitive protein binding assays where a label is bonded to a hapten with the label being subject to enzymatic transformation to produce a signal. Antibody bound to the hapten inhibits the approach of enzyme to the label.

SUMMARY OF THE INVENTION

Methods and compositions are provided for use in immunoassays for the accurate determination of a member of an immunological pair i.e. ligands and ligand receptors, at concentrations down to 1 $\mu$g/ml or less. With polyepitopic ligands labeled receptors are employed, where the label is capable of modification by modifying reagents. Upon combining polyepitopic ligand, (poly(ligand analog) with haptens) labeled receptor and the modifying reagent(s), a complex is formed between the ligand and the labeled receptor which inhibits the modification of the label by the modifying reagent(s). The label outside the complex is modified, so that the observed signal is from the unmodified label in the complex and any residual signal from the modified label. By comparing the results to known standards, the concentration of ligand can be determined.

When a monoepitopic ligand is involved, a plurality of ligand analogs will be conjugated to a hub nucleus to provide a poly(ligand analog). The poly(ligand analog) will be included with the other reagents, so that a competition exists between the monoepitopic ligand and the poly(ligand analog) for the labeled receptor. The labeled receptor which binds to the poly(ligand analog) will form a complex which inhibits the modification of the label, while free labeled receptor and labeled receptor bound to the ligand will be modified. By employing known standards, the amount of monoepitopic ligand may be determined.

For receptors, the assay is carried out in substantially the same way, except that a source of ligand or ligand analog must be provided.

The compositions can be provided as kits, whereby measured amounts of the labeled antibody, and, where required, ligand or poly(ligand analog), and modifying reagent(s) are provided, particularly as dry powders or concentrated solutions which can be reconstituted as reagent solutions for use in the immunoassays.

DESCRIPTION OF THE SPECIFIC EMBODIMENTS

Method and compositions are provided for sensitive immunoassays, where reagents can be prepared without cumbersome and difficult purifications and/or isolations of antigens and antibodies. The method will normally involve bringing together an analyte and a labeled receptor (with monoepitopic analytes, a poly(ligand analog) will be employed in addition), so as to form a complex which sterically inhibits the approach of macromolecules to the label. The label is capable of providing a distinctive signal by being exposed to an agent e.g. electromagnetic radiation, usually light, or chemical reagents. After an appropriate time, a modifying agent is added which is capable of interacting with the label and modifying, preferably reducing, its distinctive signal. The agent interacts with the label and the signal from the assay medium is measured. By comparison of the determined signal to signals from assay media having known amounts of analyte, the concentration of analyte in an unknown sample may be determined.

DEFINITIONS

Analyte—the compound or composition to be measured, which may be a ligand which is mono- or polyepitopic, antigenic or haptenic, a single or plurality of compounds which share at least one common epitopic site or a receptor.

Ligand—any compound for which a receptor naturally exists or can be prepared.

Ligand analog—a modified ligand which can compete with the analogous ligand for receptor, the modification providing means to join a plurality of ligand analogs in a single molecule.

Poly(ligand analog)—a plurality of ligand analogs joined together, normally to a hub nucleus, to provide a compound having a plurality of epitopic sites capable of competing with the analogous ligand for receptor.

Label—a compound or composition capable of providing a detectable signal in conjunction with physical activation (or excitation) or chemical reagents and capable of being modified, so that the particular signal is diminished or increased.

Receptor—Any compound or composition capable of recognizing a particular spatial and polar organization of a molecule i.e. an epitopic site. Illustrative receptors include naturally occurring receptors, antibodies, enzymes or fragments thereof that contain a binding site e.g. Fab, and the like. For any specific ligand, the receptor will be referred to as anti(ligand). The receptor anti(ligand) and its reciprocal ligand form an immunological pair.

Labeled Receptor—receptor having at least one label covalently bonded to it and retaining at least one binding site.

Modifier—a macromolecule capable of physically or chemically interacting with the label to reduce the signal produced by the label.

Complex—a combination of at least one labeled receptor and one polyepitopic ligand (includes poly(ligand analog)), normally in the assay medium there being on the average at least two of one of the components in each of the complexes and frequently a total of four or more of the components bound together.

ASSAY

The subject assay is carried out in an aqueous, normally homogeneous, zone at a moderate pH, generally close to optimum label detection. The assay zone for the determination of analyte is prepared by employing an appropriately buffered aqueous solution, the unknown sample, which may have been subject to prior treatment, labeled receptor, modifier, and as appropriate poly(ligand analog) and ancillary reagents for reacting with the label to produce the detectable signal. For determination of anti(ligand) in the sample, ligand or poly(ligand analog) will normally be added. The assay zone will normally be homogeneous.

In carrying out the assay an aqueous medium will normally be employed. Other polar solvents may also be employed, usually oxygenated organic solvents of from one to six, more usually from one to four carbon atoms, including alcohols, ethers and the like. Usually, these cosolvents will be present in less than about 35 weight percent, more usually in less than about 10 weight percent.

The pH for the medium will usually be in the range from about 5 to 10, more usually in the range from about 6 to 9. Various buffers may be used to achieve the desired pH and maintain the pH during the determination. Illustrative buffers include borate, phosphate, carbonate, Tris, barbital and the like. The particular buffer employed is not critical to this invention, but in individual assays, one buffer may be preferred over another.

Moderate temperatures are normally employed for carrying out the assay and usually constant temperatures during the period of the assay will be employed. The temperatures will normally range from about 10° to 50° C., more usually from about 15° to 40° C.

The concentration of analyte which may be assayed will generally vary from about $10^{-4}$ to $10^{-15}$ M, more usually from about $10^{-6}$ to $10^{-13}$ M. Considerations such as whether the assay is qualitative, semi-quantitative or quantitative, the particular detection technique and the concentration of the analyte of interest will normally determine the concentration of the other reagents.

Receptor (antiligand) may be a mixture of labeled and unlabeled receptor, generally having from about 5 to 100% of the receptor as labeled receptor. The proportion of unlabeled receptor will depend on the nature of the label, the manner of preparation, the sensitivity of the label detection system and the like. For example, with a fluorescer label, there may be substantial self-quenching when all of the receptor is labeled, so that it is desirable to introduce a significant amount of unlabeled receptor in the assay medium.

Normally, for polyepitopic ligand analytes the concentration of total antiligand based on binding sites will be about 1–50 times either the minimum or maximum concentration of interest based on epitopic sites, usually about 1–10 times and more usually 1–3 times the maximum concentration of interest. For monoepitopic ligand analytes and receptor analytes, based on binding sites, the respective concentrations of poly(ligand analog) and labeled antiligand will have concentrations about equal to the minimum concentration of interest, normally not exceeding the maximum concentration of interest, generally not less than $10^{-4}$, more usually not less than $10^{-2}$ of the minimum concentration of interest. Concentration ranges of interest will generally vary from about $10^{-3}$ to $10^{-14}$ g/ml. For monoepitopic analytes and receptor analytes the concentration of total antiligand other than analyte will usually be up to fifty times the concentration of polyligand analog or ligand, more usually up to 10 times, most usually up to three times.

The concentration of modifier will vary widely depending on the nature of the modifier, its effectiveness in modifying the signal, its side reactions and the like. Normally, large excesses of modifier can be used to insure that the rate of modification is rapid and the concentration of modifier is not limiting. Therefore, when the modifier is not a catalyst at least stoichiometric concentrations of modifier will be used and molar excesses of 100 or more may be employed. Where the modifier is an enzyme, concentrations of at least $10^{-2}$ times Km will usually be employed. For other catalysts, the catalytic concentration will generally range from about $10^{-2}$ to $10^{-6}$ times the minimum or maximum concentration of interest.

The order of addition may vary widely. Normally, the unknown sample and labeled receptor will be combined in an appropriate medium before the introduction of the modifier. When the modifier reversibly modifies the label, the modifier and labeled receptor may be premixed. Depending on the nature of the ancillary reagents, if any, they may be added initially or with or subsequent to the addition of the modifier. After combining the unknown with the labeled receptor and, as appropriate, ligand or poly(ligand analog), the assay medium may be incubated for a sufficient time to form complexes.

The times between the various additions for the assay components and for the immunological reactions which are involved may vary widely, depending upon the particular compounds involved, the mode of addition, the concentrations involved, the binding constants of the receptors, and the like. Normally, times between additions may vary from a few seconds to many hours, usually not exceeding twelve hours, and more usually not exceeding six hours. After adding each component to the assay mixture, different incubation periods before adding the next component or taking the measurement will be involved. Since the ultimate results will be dependent upon the results obtained with standard(s) treated in substantially the same manner, and when possible in the identical manner, the particular mode and periods of time are not critical, so long as significant reproducible differentiations are obtained with varying concentrations of analyte.

Depending upon the choice of assay protocol, the equipment employed and the concentration of analyte involved, assay volumes may be as small as about 1 $\mu$l, more usually being at least 25 $\mu$l, and will usually not exceed 5 ml, more usually not exceeding about 2 ml.

In particular situations, the subject method allows for the simultaneous determination of two or more analytes, usually not more than about five analytes. By employing labels which give substantially non-interfering signals, each different label can be conjugated to a receptor for a different analyte. This embodiment is readily illustrated with fluorescers. One employs fluorescers which fluoresce by emitting light at different wavelengths. Therefore, a particular wavelength of emitted light would be associated with a particular analyte. The assay would be performed in the normal way for each analyte, except that all the reagents and sample would be included in one assay medium. The assay medium would be irradiated with light of wave lengths which correspond to the absorption bands of the different fluorescers and the amount of fluorescence from each of the fluorescers determined. By appropriate calculations the contribution to the emission spectrum of each of the fluorescers could be determined.

The same technique could be applied with other labels, but for the most part not as conveniently. With enzyme labels, the different enzymes would have to have substrates and products which were not interfering and could be independently detected. The problem of interference between labels and their associated systems will vary to lesser or greater degrees depending upon the particular label and its modifiers.

In determining anti(ligand), the procedure is the same, with the exception indicated previously, but the observed result may be an increase or decrease in the signal depending on the relative proportions of the various components. That is, the anti(ligand) may displace labeled anti(ligand) from the complex or enhance complex formation. Preferably, a protocol is employed where anti(ligand) will displace labeled anti(ligand).

In a preferred embodiment, the modifier is anti(label), that is, a receptor which specifically binds to the label, affecting the label in a variety of ways.

One effect is to inhibit the interaction of a chemical with the label. For example, with an enzyme label, antibodies to enzyme can be prepared which sterically or allosterically inhibit the enzyme. Those enzymes which become bound by anti(enzyme) will be deactivated. Another technique is to employ a label which chemically reacts with the modifier to change the chemical nature of the modifier. For example, with a redox reaction, binding of anti(label) to one of the reactants in the redox reaction will inhibit the approach of the other reactant to the label. If the label is an enzyme substrate, binding by antilabel will inhibit the enzyme catalyzed reaction. Finally as a further illustration, anti(label) may change the environment of the label, so as to change the physical characteristics of the label. With a fluorescent label, anti(fluorescer) will change the light absorption and/or emission characteristics of the fluorescer when bound to the fluorescer. Thus, by irradiating the solution with light within the absorption band of unbound fluorescer, free fluorescer will fluoresce, at a different wave length or efficiency than the bound fluorescer, allowing free and bound fluorescer to be distinguished.

The use of an anti(label) as the modifier has many advantages. It is specific for the label and will generally not be subject to interference from materials normally encountered in samples to be assayed. Furthermore, with the enzyme, the redox and the fluorescer labels, amplification can be achieved in that a single unbound label can be used to cause a plurality of measureable events. Another preferred embodiment is a fluorescent enzyme substrate which is quenched upon interaction with an enzyme.

The measurement of the detectable signal from the label will vary widely depending upon the nature of the label. The measurement will normally involve measuring electromagnetic radiation at a particular wavelength or narrow band of wavelengths in various ranges, such as radiofrequency, ultraviolet, visible, etc., although other measurements may be made e.g. electrical or microcalorimetric. For electromagnetic measurements, the absorption or emission of radiation will be involved.

Depending upon the nature of the label, various techniques may be employed. For the most part, the techniques employed will involve the absorption or emission of electromagnetic radiation. Such techniques may involve fluorescence, chemiluminescence, ultraviolet or visible light absorption, electron spin resonance, and the like.

MATERIALS

The primary components in the subject assay for analyte are: the analyte; the labelled receptor; the modifier; any ancillary reagents for the label; and, as appropriate poly(ligand analog). In addition, in the assay for anti(ligand), ligand or poly(ligand analog) will be added. The different labels allow for great variety in protocols and methods of measurement, although certain techniques will be vastly superior to other techniques. Of particular significance are those techniques which allow for amplification, that is, where a single event results in the occurrence of a plurality of events. Within this category are redox reactions and transfer reactions, which are enzymatically mediated and result in a variety of products which may be detected in a number of different ways.

ANALYTE

The ligand analytes of this invention are characterized by being monoepitopic or polyepitopic. The polyepitopic ligand analytes will normally be poly(amino acids) i.e. polypeptides and proteins, polysaccharides, nucleic acids, and combinations thereof. Such combinations or assemblages include bacteria, viruses, chromosomes, genes, mitochondria, nuclei, cell membranes, cell walls, and the like.

For the most part, the polyepitopic ligand analytes employed in the subject invention will have a molecular weight of at least about 1,000, usually 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

The wide variety of proteins may be considered as to the family of proteins having similar structural features, proteins having particular biological functions, proteins related to specific microorganisms, particularly disease causing microorganisms, etc.

The following are classes of proteins related by structure:

protamines
histones
albumins
globulins
scleroproteins
phosphoproteins
mucoproteins
chromoproteins
lipoproteins
nucleoproteins
glycoproteins
unclassified proteins, e.g. somatotropin, prolactin, insulin, pepsin A number of proteins found in the human plasma are important clinically and include:

Prealbumin
Albumin
$\alpha_1$-Lipoprotein
$\alpha_1$-Acid glycoprotein
$\alpha_1$-Antitrypsin
$\alpha_1$-Glycoprotein
Transcortin
4.6S-Postalbumin
Tryptophan-poor
  $\alpha_1$-glycoprotein
$\alpha_1$X-Glycoprotein
Thyroxin-binding globulin
Inter-$\alpha$-trypsin-inhibitor
Gc-globulin
  (Gc 1-1)
  (Gc 2-1)
  (Gc 2-2)
Haptoglobin
  (Hp 1-1)
  (Hp 2-1)
  (Hp 2-2)
Ceruloplasmin
Cholinesterase
$\alpha_2$-Lipoprotein(s)
$\alpha_2$-Macroglobulin
$\alpha_2$-HS-glycoprotein
Zn-$\alpha_2$-glycoprotein
$\alpha_2$-Neuramino-glycoprotein
Erythropoietin
$\beta$-lipoprotein
Transferrin
Hemopexin
Fibrinogen
Plasminogen
$\beta_2$-glycoprotein I
$\beta_2$-glycoprotein II
Immunoglobulin G
  (IgG) or $\gamma$G-globulin
Mol. formula:
  $\gamma_2\kappa_2$ or $\gamma_2\gamma_2$
Immunoglobulin A (IgA)
  or $\gamma$A-globulin
Mol. formula:
  $(\alpha_2\kappa_2)^n$ or $(\alpha_2\gamma_2)^n$
Immunoglobulin M
  (IgM) or $\gamma$M-globulin
Mol. formula:
  $(\mu_2\kappa_2)^5$ or $(\mu_2\gamma_2)^5$
Immunoglobulin D (IgD)
  or $\gamma$D-Globulin ($\gamma$D)
Mol. formula:
  $\delta_2\kappa_2$) or ($\delta_2\gamma_2$)
Immunoglobulin E (IgE)
  or $\gamma$E-Globulin ($\gamma$E)
Mol. formula:
  ($\epsilon_2\kappa_2$) or ($\epsilon_2\lambda_2$)
Free K and $\gamma$ light chains
Complement factors:
C'1
  C'1q
  C'1r
  C'1s
C'2
C'3
  $\beta_1$A
  $\alpha_2$D
C'4
C'5
C'6
C'7
C'8
C'9

Important blood clotting factors include:

TABLE VII
BLOOD CLOTTING FACTORS

| International designation | Name |
|---|---|
| I | Fibrinogen |
| II | Prothrombin |
| IIa | Thrombin |
| III | Tissue thromboplastin |
| V and VI | Proaccelerin, accelerator globulin |
| VII | Proconvertin |
| VIII | Antihemophilic globulin (AHG) |
| IX | Christmas factor, plasma thromboplastin component (PTC) |
| X | Stuart-Prower factor, autoprothrombin III |
| XI | Plasma thromboplastin |

TABLE VII-continued
BLOOD CLOTTING FACTORS

| International designation | Name |
|---|---|
| | antecedent (PTA) |
| XII | Hagemann factor |
| XIII | Fibrin-stabilizing factor |

Important protein hormones include:

Peptide and Protein Hormones

Parathyroid hormone
  (parathormone)
Thyrocalcitonin
Insulin
Glucagon
Relaxin
Erythropoietin
Melanotropin
  (melanocyte-stimulating
  hormone; intermedin)
Somatotropin
  (growth hormone)
Corticotropin
  (adrenocorticotropic hormone)
Thyrotropin
Follicle-stimulating hormone
Luteinizing hormone
  (interstitial cell-stimulating
  hormone)
Luteomammotropic hormone
  (luteotropin, prolactin)
Gonadotropin
  (chorionic gonadotropin)

Tissue Hormones

Secretin
Gastrin
Angiotensin I and II
Bradykinin
Human placental lactogen

Peptide Hormones from the Neurohypophysis

Oxytocin
Vasopressin
Releasing factors (RF)
  CRF, LRF, TRF, Somatotropin-RF,
  GRF, FSH-RF, PIF, MIF Other polymeric materials of interest are mucopolysaccharides and polysaccharides.

Illustrative antigenic polysaccharides derived from microorganisms are as follows:

| Species of Microorganisms | Hemosensitin Found in |
|---|---|
| *Streptococcus pyogenes* | Polysaccharide |
| *Diplococcus pneumoniae* | Polysaccharide |
| *Neisseria meningitidis* | Polysaccharide |
| *Neisseria gonorrhoeae* | Polysaccharide |
| *Corynebacterium diphtheriae* | Polysaccharide |
| *Actinobacillus mallei;* | Crude extract |
| *Actinobacillus whitemori* | |
| *Francisella tularensis* | Lipopolysaccharide |
| | Polysaccharide |
| *Pasteurella pestis* | |
| *Pasteurella pestis* | Polysaccharide |
| *Pasteurella multocida* | Capsular antigen |
| *Brutella abortus* | Crude extract |
| *Haemophilus influenzae* | Polysaccharide |
| *Haemophilus pertussis* | Crude |
| *Treponema reiteri* | Polysaccharide |
| *Veillonella* | Lipopolysaccharide |
| *Erysipelothrix* | Polysaccharide |
| *Listeria monocytogenes* | Polysaccharide |
| *Chromobacterium* | Lipopolysaccharide |
| *Mycobacterium tuberculosis* | Saline extract of 90% phenol extracted mycobacteria and polysaccharide fraction of cells and tuberculin |
| *Klebsiella aerogenes* | Polysaccharide |
| *Klebsiella cloacae* | Polysaccharide |
| *Salmonella typhosa* | Lipopolysaccharide, Polysaccharide |
| *Salmonella typhi-murium;* | Polysaccharide |
| *Salmonella derby* | |
| *Salmonella pullorum* | |
| *Shigella dysenteriae* | Polysaccharide |
| *Shigella flexneri* | |
| *Shigella sonnei* | Crude, polysaccharide |
| *Rickettsiae* | Crude extract |
| *Candida albicans* | Polysaccharide |
| *Entamoeba histolytica* | Crude extract |

The microorgaisms which are assayed may be intact, lysed, ground or otherwise fragmented, and the resulting composition or portion, e.g. by extraction, assayed. Microorganisms of interest include:

Corynebacteria
Corynebacterium diptheriae

Pneumococci
Diplococcus pneumoniae

Streptococci
Streptococcus pyogenes
Streptococcus salivarus

Staphylococci
Staphylococcus aureus
Staphylococcus albus

Neisseriae
Neisseria meningitidis
Neisseria gonorrheae

| Enterobacteriaciae | |
|---|---|
| *Escherichia coli* <br> *Aerobacter aerogenes* <br> *Klebsiella pneumoniae* | } The coliform bacteria |
| *Salmonella typhosa* <br> *Salmonella choleraesuis* <br> *Salmonella typhimurium* | } The Salmonellae |
| *Shigella dysenteriae* <br> *Shigella schmitzii* <br> *Shigella arabinotarda* <br> *Shigella flexneri* <br> *Shigella boydii* <br> *Shigella Sonnei* | } The Shigellae |
| Other enteric bacilli | |
| *Proteus vulgaris* <br> *Proteus mirabilis* <br> *Proteus morgani* <br> *Pseudomonas aeruginosa* <br> *Alcaligenes faecalis* <br> *Vibrio cholerae* | } Proteus species |
| Hemophilus-Bordetella group | |
| *Hemophilus influenzae,* | H. ducreyi <br> H. hemophilus <br> H. aegypticus <br> H. paraiufluenzae |

-continued

*Bordetella pertussis*

Pasteurellae

Pasteurella pestis
Pasteurella tulareusis

Brucellae

Brucella melitensis
Brucella abortus
Brucella suis

Aerobic Spore-forming Bacilli

Bacillus anthracis
Bacillus subtilis
Bacillus megaterium
Bacillus cereus

Anaerobic Spore-forming Bacilli

Clostridium botulinum
Clostridium tetani
Clostridium perfringens
Clostridium novyi
Clostridium septicum
Clostridium histolyticum
Clostridium tertium
Clostridium bifermentans
Clostridium sporogenes

Mycobacteria

Mycobacterium tuberculosis hominis
Mycobacterium bovis
Mycobacterium avium
Mycobacterium leprae
Mycobacterium paratuberculosis

Actinomycetes (fungus-like bacteria)

Actinomyces israelii
Actinomyces bovis
Actinomyces naeslundii
Nocardia asteroides
Nocardia brasiliensis

The Spirochetes

*Treponema pallidum*     *Spirillum minus*
*Treponema pertenue*     *Streptobacillus moniliformis*
*Treponema carateum*
*Borrelia recurrentis*
*Leptospira icterohemorrhagiae*
*Leptospira canicola*

Mycoplasmas

Mycoplasma pneumoniae

Other pathogens

Listeria monocytogenes
Erysipelothrix rhusiopathiae
Streptobacillus moniliformis
Donvania granulomatis
Bartonella bacilliformis

Rickettsiae (bacteria-like parasites)

Rickettsia prowazekii
Rickettsia mooseri
Rickettsia rickettsii
Rickettsia conori
Rickettsia australis
Rickettsia sibiricus
Rickettsia akari
Rickettsia tsutsugamushi
Rickettsia burnetii
Rickettsia quintana Chlamydia (unclassifiable parasites bacterial/viral)

Chlamydia agents (naming uncertain)

Fungi

*Cryptococcus neoformans*
*Blastomyces dermatidis*
*Histoplasma capsulatum*
*Coccidioides immitis*
*Paracoccidioides brasiliensis*
*Candida albicans*
*Aspergillus fumigatus*
*Mucor corymbifer (Absidia corymbifera)*
*Rhizopus oryzae*
*Rhizopus arrhizus* } Phycomycetes
*Rhizopus nigricans*
*Sporotrichum schenkii*
*Fonsecaea pedrosoi*
*Fonsecaea compacta*
*Fonsecaea dermatitidis*
*Cladosporium carrionii*
*Phialophora verrucosa*
*Aspergillus nidulans*
*Madurella mycetomi*
*Madurella grisea*
*Allescheria boydii*
*Phialosphora jeanselmei*
*Microsporum gypseum*
*Trichophyton mentagrophytes*
*Keratinomyces ajelloi*
*Microsporum canis*
*Trichophyton rubrum*
*Microsporum andouini*

Viruses

Adenoviruses

Herpes viruses

Herpes simplex
Varicella (Chicken pox)
Herpes Zoster (Shingles)
Virus B
Cytomegalovirus

Pox Viruses

Variola (smallpox)
Vaccinia
Poxvirus bovis
Paravaccinia
Molluscum contagiosum

Picornaviruses

Poliovirus
Coxsackievirus
Echoviruses
Rhinoviruses

Myxoviruses

Influenza (A, B, and C)
Parainfleuenza (1–4)
Mumps Virus
Newcastle Disease Virus
Measles Virus Rinderpest Virus
Canine Distemper Virus
Respiratory Syncytial Virus
Rubella Virus

Arboviruses

Eastern Equine Eucephalitis Virus
Western Equine Eucephalitis Virus
Sindbis Virus
Chikungunya Virus
Semliki Forest Virus
Mayora Virus
St. Louis Encephalitis Virus
California Encephalitis Virus
Colorado Tick Fever Virus
Yellow Fever Virus
Dengue Virus

Reoviruses

Reovirus Types 1-3

Hepatitis

Hepatitis A Virus
Hepatitis B Virus

Tumor Viruses

Rauscher Leukemia Virus
Gross Virus
Maloney Leukemia Virus

The monoepitopic ligand analytes will generally be from about 100 to 2,000 molecular weight, more usually from 125 to 1,000 molecular weight. The analytes of interest include drugs, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which includes cocaine and benzoyl ecgonine, their derivatives and metabolites; ergot alkaloids, which includes the diethylamide of lysergic acid; steroid alkaloids; iminazoyl alkaloids; quinazoline alkaloids; isoquinoline alkaloids; quinoline alkaloids; which includes quinine and quinidine; diterpene alkaloids, their derivatives and metabolites.

The next group of drugs includes steroids, which includes the estrogens, gestrogens, androgens, andrenocortical, bile acids, cardiotonic glycosides and aglycones, which includes digoxin and digoxigenin, saponins and sapogenins, their derivatives and metabolites. Also included are the steroid mimetic substances, such as diethyl stilbestrol.

The next group of drugs is cyclic lactams having from 5 to 6 membered rings, which include the barbiturates, diphenyl hydantoin, and their metabolites.

The next group of drugs is aminoalkyl benzenes, with alkyl of from 2 to 3 carbon atoms, which includes the amphetamines, catecholamines, which includes ephedrine, L-dopa, epinephrine, narceine, papaverine, their metabolites and derivatives.

The next group of drugs is benzheterocyclics which include oxazepam, chlorpromazine, tegretol, imipramine, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs includes the vitamins such as A, B, C, D, E and K.

The next group of drugs is prostaglandins, which differ by the degree and sites of hydroxylation and unsaturation.

The next group of drugs is antibiotics, which include penicillin, chloromycetin, actinomycetin, tetracycline, terramycin, gentamicin, tobramycin, adriamycin their metabolites and derivatives.

The next group of drugs is the nucleosides and nucelotides, which include ATP, NAD, FMN, adenosine, guanosine, thymidine, and cytidine with their appropriate sugar and phosphate substituents.

The next group of drugs is miscellaneous individual drugs which include methadone, meprobamate, serotonin, meperidine, amitriptyline, nortriptyline, lidocaine, procaineamide, acetylprocaineamide, propanolol, griseofulvin, butyrophenones, antihistamines, anticholinergic drugs, such as atropine, their metabolites and derivatives.

The next group of compounds is amino acids and small peptides which include thyroxine, triiodothyronine, oxytocin, ACTH, angiotensin, met- and leu-enkephalin their metabolites and derivatives.

Metabolites related to diseased states include spermine, galactose, phenylpyruvic acid, porphyrin type 1, vanillomandelic acid, epinephrine and norepinephrine Among pesticides of interest are polyhalogenated biphenyls, phosphate esters, thiophosphates, carbamates, polyhalogenated sulfenamides, their metabolites and derivatives.

For receptor analytes, the molecular weights will generally range from 10,000 to $2 \times 10^6$, more usually from 10,000 to $10^6$. For immunoglobulins IgA, IgG, IgE and IgM, the molecular weights will generally vary from about 150,000 to about $10^6$. Enzymes will normally range from about 10,000 to 600,000 in molecular weight. Natural receptors vary widely, generally being at least about 15,000 molecular weight and may be $10^6$ or higher molecular weight, including such materials as avidin, thyroxine binding globulin, thyroxine binding prealbumin, transcortin, etc.

Poly(ligand analog)

For monoepitopic analytes, it is necessary to prepare a polyepitopic composition having a plurality of epitopic sites capable of competing with the ligand. This normally involves modification of the ligand to provide for a linking group between the ligand and a hub nucleus, normally a water soluble polymer and conveniently a poly(amino acid).

The hub nucleus will generally be at least about 2,000, usually from about 25,000 to 600,000 molecular weight, more usually from about 30,000 to 300,000 molecular weight. The linking group may be a bond, but will more conveniently be a divalent organic group, usually aliphatic having not more than one site of ethylenic unsaturation, having from 0 to 6, more usually from 1 to 4 and preferably from about 1 to 2 heteroatoms, which are oxygen, nitrogen and sulfur, preferably oxygen and nitrogen, wherein oxygen is bonded solely to carbon as oxy(ether) or nonoxocarbonyl and nitrogen is bonded to carbon e.g. tertiary-amino or as amido, while sulfur is analogous to oxygen.

The functionalities involved in linking normally include alkylamine, amide, amidine, thioamide, urea, thiourea, guanidine, azo, thioethers and sulfonamide.

Illustrative functionalities involved in linking are carboxylic acids in conjunction with diimides, mixed anhydrides with carbonate monoesters, aldehydes in conjunction with reductants e.g. borohydrides, imidoesters, active carboxylic esters e.g. N-hydroxy succinimide or p-nitrophenyl, isocyanates, isothiocyanates, active halide, and the like.

Normally, the monoepitopic ligand will be modified to introduce a group which is active or activatable, followed by combining the modified ligand with the hub molecule so as to polysubstitute the hub molecule. Normally, there will be at least one ligand molecule per 50,000 molecular weight of the hub molecule, more usually at least one per 25,000 molecular weight and usually not more than one per 1,500 molecular weight. Illustrative hub molecules include albumins, globulins, cellulose, dextran, and the like. That is, those compositions which have active functionalities such as amino and hydroxyl, which can be readily substituted and remain soluble in an aqueous solution.

For an extensive discussion of linking groups for haptens to poly(amino acids) see U.S. Pat. No. 3,817,837, the appropriate portions of which are incorporated herein by reference.

Labels and Modifiers

There are a number of requisites for an appropriate label. The first requisite is that the label is capable of being conjugated to a receptor. As conjugated, the label must be capable of producing a detectable signal when the receptor is bound to analyte. Third, the label must be capable of modification by a macromolecular compound or composition, so as to modify the signal preferably by diminishing the signal to be measured. In addition, desirable labels are stable, are not subject to interference by materials present in the assay medium other than the modifier, will not insolubilize the receptor, provide a signal which is subject to amplification, that is, for each label a plurality of events can be measured and ultimately provides a signal which can be electronically detected or alternatively an extremely sensitive detection system is available.

The modifier must be of sufficient size to be inhibited from interacting with the label, when the labeled receptor is bound to ligand or poly(ligand analog). The modifier, obviously, will vary with the particular label. Therefore, there is no simple definition of a modifier. The modifier may interact physically with the label, changing the environment about the label where the environment affects the signal. Alternatively, the modifier may react chemically with the label, so as to change the chemical nature of the label, with a resultant change in the signal. Chemical modification may be carried out in one or two stages. In a one stage situation, the modifier will react with the label on labeled receptor which is not bound to analyte, leaving label on labeled receptor bound to analyte substantially unaffected and capable of providing the measured signal. In a two stage method, the modifier will effectively destroy the ability of label on free labeled receptor (unbound to analyte) to subsequently give a signal, followed by addition of a low molecular weight reagent which reacts with the label to provide the desired signal. As individual examples are given the significance of the general description will become more evident.

The manner in which the modifier is inhibited from interacting with the label involved in the complex can be achieved in a variety of ways. In some instances the modifier will naturally occur as a macromolecule e.g. antibodies or enzymes. Alternatively, one could bond compounds capable of modifying the label, which are of small size, usually less than 1,000 molecular weight, to a large molecule, greater than 5,000 molecular weight, by covalent or ionic bonds. Another technique would be to provide for noncovalent, either specific or non-specific, binding to a large molecule e.g. protein, particularly globulins and albumins.

Enzyme label and modifiers

Enzymes are particularly useful as labels, since they provide amplification, in that a single active enzyme can act on a plurality of substrate molecules over a short period of time. Furthermore, the conjugation of enzymes to antibodies is well known and has received ample illustration in the literature. In addition, techniques for measuring enzymes providing spectrophotometric signals are well established. A wide variety of enzymes are commercially available and have been extensively characterized.

There are a number of criteria in the choice of an enzyme. Most importantly, a convenient modifier is available. Preferably, the modifier deactivates the enzyme, although activation can also be employed. In addition, the change in activity, if any, upon binding to ligand should be augmented by the modifier. Also, the enzyme should retain a substantial proportion of its original activity, preferably greater than 30% upon conjugation to receptor. The enzyme substrates will usually be smaller than the modifier in order to penetrate the complex, although considerations other than molecular weight affect the availability of the substrate in the complex; the enzymes will preferably have low molecular weight substrates, usually under 5,000 molecular weight, more usually under about 2,000 molecular weight and preferably under about 1,000 molecular weight.

Other considerations include turnover number, long term stability in storage, and that the enzyme is not significantly adversely affected by materials other than the modifier in the assay medium.

Of the various enzymes, the following table indicates enzymes of particular interest set forth in accordance with the I.U.B. classification.

1. Oxidoreductases
  1.1 Acting on the CH—OH group of donors
    1.1.1 With NAD or NADP as acceptor
      1. alcohol dehydrogenase
      6. glycerol dehydrogenase
      26. glyoxylate reductase
      27. L-lactate dehydrogenase
      37. malate dehydrogenase
      49. glucose 6-phosphate dehydrogenase
      17. mannitol 1-phosphate dehydrogenase
    1.1.2 With cytochrome as an acceptor
      3. L-lactate dehydrogenase
    1.1.3 With $O_2$ as acceptor
      4. glucose oxidase
      9. galactose oxidase
  1.2 Acting on the CH—$NH_2$ group of donors
    1.4.3 With $O_2$ as acceptor
      2. L-amino acid oxidase
      3. D-amino acid oxidase
  1.6 Acting on reduced NAD or NADP as donor
    1.6.99 With other acceptors diaphorase
  1.10 Acting on diphenols and related substances as donors
    1.10.3 With $O_2$ as acceptor
      1. polyphenol oxidase
      3. ascorbate oxidase -continued 1.11 Acting on H$_2$O$_2$ as acceptor
  1.11.1
    6. catalase
    7. peroxidase
3. Hydrolases
  3.1 Acting on ester bonds
    3.1.1 Carboxylic ester hydrolases
      7. cholinesterase
    3.1.3 Phosphoric monoester hydrolases
      1. alkaline phosphatase
    3.1.4 Phosphoric diester hydrolases
      3. phospholipase C
  3.2 Acting on glycosyl compounds
    3.2.1 Glycoside hydrolases
      1. α-amylase
      4. cellulase
      17. lysozyme
      23. β-galacotsidase
      27. amyloglucosidase
      31. β-glucuronidase
  3.4 Acting on peptide bonds
    3.4.2 Peptidyl-amino acid hydrolase
      1. carboxypeptidase A
    3.4.4 Peptidyl-peptide hydrolase
      5. α-chymotrypsin
      10. papain
  3.5 Acting on C-N bonds other than peptide bonds
    3.5.1 In linear amides
      5. urease
  3.6 Acting on acid anhydride bonds
    3.6.1 In phosphoryl-containing anhydrides
      1. inorganic pyrophosphatase
4. Lyases
  4.1 Carbon-carbon lyases
    4.1.2 Aldehyde lyases
      7. aldolase
  4.2 Carbon-oxygen lyases
    4.2.1 Hydrolases
      1. carbonic anhydrase
  4.3 Carbon-nitrogen lyases
    4.3.1 Ammonia lyases
      3. histidase The enzymic modifiers may be divided into two classes: those that affect the enzyme by physical interaction; and those that affect the enzyme by chemical interaction. A convenient and simple macromolecular enzyme modifier that affects the enzyme by physical interaction is an anti(enzyme). These are antibodies which bind to the enzyme and modify, most usually diminish or destroy the enzyme activity. Many anti(enzymes) which provide this modification of activity are commercially available and others can be produced by employing enzymes as antigens in an appropriate vertebrate. Because of the large nature of antibodies, the antibodies will be inhibited from binding to enzyme-labeled receptors which are bound to ligands of any significant size. Therefore, those enzymes bound to free enzyme labeled receptors will be more readily bound by anti(enzyme) and have altered activity.

In carrying out the assay, one would normally combine the unknown suspected of containing the analyte and enzyme labeled receptor and incubate the assay medium for a time sufficient to form complexes. One would then add anti(enzyme) and have a second incubation which will allow for the anti(enzyme) to bind to available enzyme. Alternatively the two antibodies can be added simultaneously. The enzyme substrates can be added concomitantly with the addition of the anti(enzyme) or preferably subsequent to the incubation of the anti(enzyme) in the assay medium. A normal enzyme assay may then be carried out.

Another technique for physical interaction is to provide a receptor for a prosthetic group e.g. a coenzyme, which can favorably complete with the enzyme for the prosthetic group. For example avidin will strongly bind to biotin which is a cofactor with ATP-dependent carboxylation enzyme reactions illustrated by methyl malonyl-oxalacetic transcarboxylase. The biotin is covalently attached to the enzyme. With other prosthetic groups which are not covalently bonded, affinity labeling would be required. By including avidin in the assay medium which can bind to the biotin, avidin could bind to the biotin bound to the enzyme inhibiting the enzyme. Thus the enzyme outside of the complex would be inhibited.

For chemical interaction, reagents will be used which will react chemically with the enzyme, normally to inhibit its activity, although activation is also feasible. There are a number of different ways for inhibiting enzymatic activity. Nonspecific reagents can be employed which are specific, however, for a specific functionality e.g. mercapto or hydroxyl (serine enzymes) groups. Where the enzyme group has a mercapto or hydroxyl group as part of its active site and essential to the enzymatic reaction, by having the reagent react with the active site, the enzyme becomes totally inhibited. These inhibitors could be added at the same time as adding substrate, where the inhibitor would compete with substrate for the active site or preferably be added before the addition of substrate, so as to avoid the competition. Illustrative inhibitors of this type are phosphoryl halide esters, which inhibit trypsin, cholinesterase, and phosphoglucomutase by reacting with the serine hydroxyl, aryl organomercurial halides, which react with the mercapto group of cysteine, trivalent arsenicals, with inhibit pyruvate α-ketoglutarate dehydrogenases and dihydrolipoate, iodoacetate esters which react with the mercapto group cysteine, such as with glyceraldehyde-P-dehydrogenase, and the like.

A number of different irreversible inhibitors (inactivators) specific for particular enzymes are known and may be employed to the extent that they can be derivatized to macromolecular hub molecules and retain their activity. The following table indicates a number of known inhibitors.

| Enzyme | Inhibitor |
| --- | --- |
| γ-cystathionase | 2-amino-4-pentinoic acid (I) |
|  | 2-amino-4-chloro-4-pentenoic acid (II) |
|  | 3-3-dichloroalanine (III) |
|  | 3,3,3,-trichloroalanine (IV) |
| alanine racemase | (IV) |
|  | D-cycloserine |
| tryptophanase | (IV) |
| tryptophan synthase (β$_2$) & (α$_2$β$_2$) | (IV) |
| lactate oxidase | 2-hydroxyl-3-butinoic acid |
| monoamine oxidase | N,N-trimethyl 2-propinylamine |
|  | β-aminopropionitrile |
| plasma amine oxidase | 2-bromoethylamine |
|  | 2-propinylamine |
|  | 2-chlorallylamine |
|  | phenyl glycine |
|  | p-nitrophenyl glycine |
|  | aminoacetonitrile |
| β-cystathionase | (IV) |
|  | 2-amino-3-hydroxypropyl-1 3'-carboxy-3'-amino-1'-propenyl-1 ether |
| aspartate aminotransferase | L-2-amino-4-methoxy-trans-3-butenoic acid |
| γ-aminobutyric acid-α-ketoglutarate transaminase | ethanolamine O-sulfate |
| formylglycinamid ribonucleotide amidotrans- | |

| Enzyme | Inhibitor |
|---|---|
| ferase | albiziin |
|  | azaserine |
|  | diazooxonorleucine |
|  | diazooxonanorvaline |
| traspeptidase (membrane bound) | 6-aminopenicillanic acid |
|  | $\Delta^3$-7-aminocephalosporinic acid |
| B$_6$-linked enzymes | mimosine |
| serine protease | physostigime |
| glutamine snythetase | methionine sulfoximine |
|  | wildfire toxin |
| nucleotide requiring enzymes e.g. malate dehydrogenase and lactate dehydrogenase | Blue Dextran (Wilson, Biochem. and Biophys. Res. Comm. 72, 816 (1976) |
| peroxidase | o-dianisidine-dextran |

While competitive reversible inhibitors can be employed, these are not preferred, since they will be competing with substrate for enzyme with varying degrees of effectiveness in reducing the enzymatic rate of enzymes present in unbound enzyme labeled receptor.

Besides the specific enzymes listed above there will be many related enzymes which can be inactivated by the same irreversible inhibitors. Also, many derivatives of the irreversible inhibitors can be prepared which will be capable of inhibition, by retention of the active portion of the molecule.

Illustrative examples of inhibitors conjugated to a protein and the inhibited enzyme are as follows:

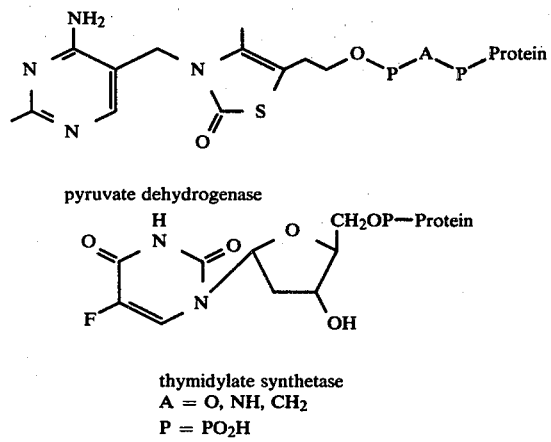

pyruvate dehydrogenase thymidylate synthetase
A = O, NH, CH$_2$
P = PO$_2$H

Where the inhibitor is not a macromolecule, that is a molecule having at least a molecular weight greater than 2,000, normally greater than 5,000, the inhibitor will be conjugated to a hub nucleus to provide the necessary size to inhibit its approach to the complex. In conjugating the inhibitor to a hub nucleus, a site for linking will be chosen distant from the portion of the inhibitor which is involved in the inhibition. It will therefore normally be preferable to employ inhibitors which have sites which are not critical to the inhibition and act with enzymes which are not too specific in their structural requirements for substrates. Modes of linking have already been discussed for the poly(ligand analog), as well as hub nuclei, which discussion is applicable here.

In carrying out the assay for the remaining enzyme activity, enzyme substrates and cofactors are added and the change in concentration of one of the substrates or cofactors monitored. This is conveniently done by having a substrate or cofactor which undergoes a change in its light absorptive characteristics by virtue of the enzymatic reaction. In some instances it may be desirable to couple the product of the enzyme label with another enzyme, which produces a readily detectable product.

Fluorescent label and modifiers

Various fluorescent labels may be employed, such as umbelliferone, fluoresceins, rhodamines, and naphthylamino compounds, e.g. 1-dimethylaminonaphthyl-5-sufonate(Dansyl). The fluorescers which are employed will normally absorb light at wavelengths in excess of 300 nm, usually in excess of 350 nm, and preferably in excess of 400 nm. These fluorescers may be readily conjugated to antibodies by a variety of methods. See in particular U.S. Pat. No. 3,996,345, the appropriate portions of which are incorporated herein by reference.

A wide variety of different techniques exist for modifying fluorescence. Anti(fluorescers) can be employed, which when bound to fluorescer substantially modify, usually diminish, fluorescence of the fluorescer. See particularly U.S. Pat. No. 3,998,943 which describes this phenomenon. Alternatively, one could use quencher labeled anti(receptor), which is capable of binding to fluorescer labeled receptor which is not bound to analyte. The quencher would quench the fluorescence of fluorescers outside the complex. Finally, one could use enzymes or chemical reagents which would react with the fluorescer to modify its absorption characteristics and/or destroy its fluorescence capability. Of particular interest as chemical reagents are various peracids, either inorganic or organic, which can be linked to a soluble support to provide the macromolecular modifier. Preferred enzymes include hydrolases, such as phosphatases and glycosidases which can act on the fluorescer to modify the fluorescence.

In carrying out the assay, the analyte and as appropriate ligand or poly(ligand analog) would be combined with fluorescer labeled receptor and incubated for a sufficient time to form complexes. The modifier would then be added and the assay medium irradiated at a wavelength within the absorption spectrum of the fluorescer.

Chemiluminescent label and modifier

Various chemiluminescent substances may be employed, such as the 1,4-phthalazinediones, e.g. luminol(5-amino-2,3-dihydro-1,4-phthalazinedione), 6,7,8-trimethoxyluminol and 9-dimethylamino benzo[H]-1,4-phthalazinedione; lophine, lucigenin, N-methyl 9-acylacridinum halides, luciferins, and the like. See McCapra, Quarterly Reviews 20 485 (1966).

The assay could be carried out by combining the analyte and as appropriate, ligand or poly(ligand analog) and allowing a sufficient time for complex formation. The reagents necessary for chemiluminescence could then be added which would react with the chemiluminescers which are not involved in complexes. These reagents are normally oxidants such as hydrogen peroxide, organic hydroperoxides, e.g. peracids, inorganic peroxides, e.g. Oxone, oxygen, and the like. The reagents would be employed as a macromolecular reagent formed in manners previously described or alternatively employing an enzyme mediated chemiluminescence system. With the enzyme system, the enzyme will be inhibited from reacting with chemiluminescers involved in the complex and these would be protected from reaction. After a sufficient time for destruction of the chemiluminescence outside of the complex, either a small reagent could be employed for reacting with the chemiluminescers inside the complex or the conditions of the assay medium could be changed, so as to break up the complex and free the chemiluminescers. The chemiluminescence could then be measured by employing the appropriate substrates and conditions. Only the chemiluminescence of the chemiluminesers originally in the complex would be measured.

Chemiluminescence can be measured with a photometer or a scintillation counter.

Illustrative reactions include: luciferin, oxygen, and luciferase; luciferin, hydrogen peroxide and luciferase; luminol, hydrogen peroxide and horseradish peroxidase; and luminol and hydrogen peroxide.

Stable free radical label and modifiers

Stable free radicals include nitroxides, verdazyls, nitronyl nitroxides, and the like. For a general discussion of stable free radicals see Forrester, *Organic Chemistry of Stable Free Radicals,* Academic Press, New York (1968). The stable free radicals of particular interest are the cyclic nitroxides of from 5 to 6 annular members, which are tetrasubstituted by alkyl groups of from 1 to 3 carbon atoms in the $\alpha$ positions. Various reductants may be employed which when attached to macromolecules will reduce the stable free radicals which are not involved in the complex. Illustrative reductants include dithioerythritol, glutathione, ascorbic acid, dialkylhydroxylamines, etc.

The residual free radicals which are involved in the complex can be measured in an electron spin resonance spectrometer.

Light absorptive label and modifiers

Compounds which absorb light in the ultraviolet or visible region can be employed, normally having absorption maxima greater than 300 Å, more usually greater than 350 Å, preferably greater than 400 Å. A large number of dyes can undergo a change in their absorption spectra upon binding to a receptor can others be readily reduced or oxidized to go from a colorless form to a colored form. Illustrative dyes include safranin, 2,6-dichlorophenol-indophenol, methylene blue, brilliant cresyl blue, phenazine methosulfate, Meldola blue, and the like. For the most part, only concentrations down to about $10^{-6}$ M are detectable, so that light absorptive compounds would only be useful where relatively high concentrations of analyte are encountered.

In carrying out the assay, one would incubate the dye labeled receptor with the analyte and as appropriate, ligand or poly(ligand analog), for a sufficient time to form complexes, followed by adding an appropriate macromolecular oxidant or reductant to change the dyes not involved in the complex to their leuco form.

Redox labels and modifiers

Various reductants and oxidants can be employed which may be dyes (as described prevously) or may provide a product which reacts with a dye. Of particular interest is where the redox reaction involves three materials which can be involved in cycling, where two of the materials cannot react or react only slowly without the intermediacy of the other material. For example, NADH, NADPH, and other dihydro-1,4-pyridines e.g. Hanztsch ester, can be employed to reduce quinonediimines e.g. Meldola blue and phenazine methosulfate, which will then react with a dye such as thiazolium blue.

By employing a receptor for one of the reactants in the redox reaction, particularly the intermediate reactant, the reaction could be inhibited where the redox reactant labeled receptor is not involved in the complex.

In carrying the assay out, the analyte and as appropriate ligand or poly(ligand analog) would be combined and allowed to proceed to complex formation. The receptor for the redox reactant could then be added or other modifier e.g. reductant or oxidant, followed by the addition of any other reagents. In the cycling embodiment employing two reactants, both a reductant and an oxidant would be added.

Kits

In performing assays it is a matter of substantial convenience, as well as providing significant enhancement in accuracy to provide the reagents combined in a kit. In developing an assay, the ratio of reagents is optimized to provide for highest sensitivity and reproducibility over the range of interest. This ratio is referred to as the loading factor. The particular ratio is related to the response of the reagents in providing the detectable signal to changes in the concentration of the analyte over the concentration range of interest. There is the further consideration that since one is dealing with extremely small amounts of materials, more accurate measurement can be obtained at a central controlled source, where the materials are measured for a plurality of assays.

In providing a kit, the materials are offered as dry powders, lyophilized as necessary, or as concentrated solutions or as dilute ready to use solutions. The reagents are reconstituted or diluted to a specific volume, if required, which allows for accurate transfer and a predetermined final concentration and ratio of reagents.

Furthermore, it is desirable to combine as many reagents as possible in a single vessel for each step of the assay. Normally, the members of an immunological pair will not be combined. An exception is the use of Fab fractions as the receptor which allows for the combination of the members of an immunological pair. Another consideration is that the reagents should not adversely interact once diluted, as would occur between an enzyme and its substrates (including cofactors). Obviously, when a plurality of substrates are required, only one need be omitted to prevent the enzymatic reaction.

Besides the reagents necessary for the assay, there will normally be other additives. Buffer will normally be provided as an adjunct reagent, although buffers may be included with one or more of the active reagents. Various stabilizers and preservatives may be included. Illustrative of such materials are proteins, such as serum albumin, gelatin, and egg albumin; polyols, such as glycerol and mono- and polysaccharides, e.g. guar gum and mannose; surfactants; preservatives, such as EDTA, sodium azide and the like. The amount of protein or mono- or polysaccharide employed will be sufficient to provide a final concentration in the reagent solution of from about 0.05 to 10 mg/ml. The glycerol may be used in amounts of up to 40% by weight. The other reagents will generally vary widely in amounts to provide from about 0.01 to 2000 $\mu$g/ml of reagent solution.

For all of the assays, the reagents can be individually provided. When Fab receptors are employed, the Fab may be combined with its complementary immunological pair member. Also, the combination of reagents will depend on whether a competitive or equilibrium mode is employed for binding of the receptors to ligand.

The following table indicates the likelier combinations where the label modifier is antilabel.

Table

| | |
|---|---|
| (1) $ab_{li}$-La | $ab_{1a}$ mod. reagents (ligand or plan) |
| (2) $ab_{li}$-La | $ab_{1a}$ + mod. reagents |
| (3) $ab_{li}$-La + $Fab_{1a}$ | mod. reagents (ligand or plan) |
| (4) $Fab_{li}$-La + $Fab_{1a}$ + | (ligand or plan) mod. reagents |
| $ab_{li}$-La | labeled receptor |
| | li-ligand |
| | $ab_{li}$-antiligand |
| | La-label |
| $ab_{1a}$ | antilabel |
| | la-label |
| $Fab_{li}$-La | labeled receptor |
| $Fab_{li}$ | Fab fragment receptor for ligand |
| $Fab_{1a}$ | Fab fragment for label |
| plan | polyligand analog |
| mod. reagents | modifier reagents e.g. substrates and reactants |

Where the modifier is not an antilabel, then modes (1) and (2) would be employed, where the $ab_{1a}$ is substituted by the appropriate modifier.

EXPERIMENTAL (All temperatures not otherwise indicated are in centigrade. All percents and parts not otherwise indicated are by weight, except for mixtures of liquids which are by volume. Unless otherwise indicated, materials employed in the various reactions are commercially available.)

EXAMPLE 1.

Conjugation of horseradish peroxidase (HRP) to anti(human IgG) (anti(hIgG))

Into a dialysis bag was introduced 4 ml of 8.5 mg/ml of anti(hIgG, $F_c$ specific) (Dako Lot No. 015, titer 600 μg/ml. and dialyzed against 3×350 ml of 0.1 M sodium phosphate buffer (pH 7.5) in a cold room (2°-4°). The residue was diluted with 5.1 ml of the dialysate and spun down for 10 mins at 15,000 rpm at 2°-4°.

Into a 10 ml RB flask was charged 5 ml (32.3 mg) of 6.45 mg/ml anti(hIgG) prepared above, cooled in an ice bath and 15 μl of 1.5×10$^{-2}$ M [$^{14}$C] acetic anhydride-benzene solution added with stirring. After 2.75 hrs., the reaction was quenched by the addition of an aqueous solution of 2 M hydroxylamine and 2 M NaCl, the ice bath removed and the mixture stirred at room temperature for 1 hr. After dialyzing against 1×350 ml of 0.1 M sodium phosphate and 0.1 M sodium sulfate (ph 7.1), the residue was chromatographed on a 2×44 cm G-25 M gel swollen with the above dialysis buffer and eluted with the same buffer. Flow rate was 10 drops/min 36 ml/hr and 2.4 ml fractions were collected. Fractions containing radioactivity were combined to give a total volume of 23 ml, containing 31.5 mg of anti(hIgG). A 22.5 ml portion (30.8 mg) of the anti(hIgG) was transferred to a dialysis bag and dialysized 3×1 l. of ice cold 50% saturated ammonium sulfate in the cold room.

Horseradish peroxidase (Sigma VI, Lot No. 65C-9530) was dissolved in saturated ammonium sulfate to provide a solution containing 6.5 mg/ml and a 1 ml aliquot was spun down for 4 min. in a cold room, the supernatant discarded, and the pellet redissolved in 5 ml of ice cold 0.3 M sodium bicarbonate (pH 8.5) and dialyzed 3×400 ml of 0.3 M sodium bicarbonate buffer (ph 8.5) in the cold room.

The dialyzed anti(hIgG) was diluted with dialysate to 17 ml to provide a concentration of 1.81 mg/ml. A 3 ml aliquot (5.4 mg) of this solution in 50% saturated ammonium sulfate was spun down at 10,000 rpm for 5 min at 2°-4°, the supernatant was discarded, the precipitate dissolved in 0.5 ml 10 mM sodium bicarbonate-sodium carbonate buffer (pH 9.5) and dialyzed 3×350 ml against the same buffer. The horseradish peroxidase residue was diluted with the dialysate to 1.1 ml. UV analysis of an aliquot showed a concentration of 6.31 mg/ml.

To 0.8 ml of the above HRP solution was added 0.2 ml of the sodium bicarbonate buffer to provide a total volume of 1 ml and 100 μl of 1% 2,4-dinitrofluorobenzene in 95% ethanol added with stirring and the mixture stirred for 1 hr. at room temperature while protected from light. To the mixture was then added dropwise 1 ml of an aqueous 30.2 mM sodium periodate solution, the mixture stirred for 0.5 hr. protected from light, followed by the addition of 1 ml of an aqueous 0.34 M ethylene glycol solution, the mixture stirred for 0.75 hr. and then dialyzed with 2×350 ml of ice cold 10 mM sodium bicarbonate-sodium carbonate buffer (pH 9.5).

To a reaction flask was charged 1 ml of 4.5 mg/ml anti(hIgG) in the sodium bicarbonate-sodium carbonate buffer, followed by the horseradish peroxidase-periodate reaction product solution. The HRP/anti(hIgG)M ratio was 4.2. After stirring for 0.5 hr, 5.05 mg of sodium borohydride was added, the mixture stirred at ice bath temperature for 5.5 hours, followed by dialysis 1×350 ml of 0.1 M sodium phosphate and 0.1 M sodium sulfate (pH 7.1) and then dialyzed against aqueous saturated ammonium sulfate. The residue was spun down for 4 mins. at 2°-4°, the supernatant discarded, and the precipitate redissolved in 0.4 ml phosphate-sulfate buffer. The solution was chromatographed on a 1.5×88 cm G-200 column (gel swollen in the same buffer) and eluted with the same buffer. Flow rate was 2 drops per min. and 20 drop portions were collected. The fractions shown to absorb in the uv at 403 nm and 280 nm were pooled and the eluant dialyzed against saturated ammonium sulfate, the residue spun down at 15,000 rpm for 5 min. at 2°-4°, the supernatant discarded and the precipitate dissolved in 0.4 ml of the phosphate-sulfate buffer. This solution was chromatographed on a 1.5×88 cm G-200 column, again swollen with the same buffer, and eluted with the same buffer, with a flow rate of 2 drops/min and 20 drop fractions collected. Those fractions showing by uv absorption the presence of the desired conjugate were combined into three fractions and assayed for HRP. Each of the fractions was made 1% in egg albumin to stablize the protein. Fraction I was 4.18×10$^{-7}$ M in anti(hIgG), 5.25×10$^{-7}$ M in HRP and had a specific activity of 119 IU/mg; fraction II was 1.08×10$^{-6}$ M in anti(hIgG), 4.6×10$^{-7}$ M in HRP and had a specific activity of 309 IU/mg; fraction III was 5.1×10$^{-7}$ M in anti(hIgG), 7.56×10$^{-7}$ M in HRP and had a specific activity of 684 IU/mg.

EXAMPLE 2.

Conjugation of fluorscein to anti(human IgG) (anti(hIgG)).

To 0.5 ml of a 14 mg/ml aqueous buffered solution of rabbit anti(hIgG) (Moles 65.063, lot #R220) (carbonate, 0.1 M, pH 9.0) was added 50 μl of fluorescein isothiocyanate (4 mg/ml) in DMF and the mixture stirred at room temperature for two hours. The reaction solution was then transferred to a 0.9×25 cm Sephadex G-25 column and eluted with PBS, pH 7.8 containing 0.05% NaN$_3$. The isolated product had an average ratio of fluorscein to anti(hIgG) of about 4.4.

A number of assays were carried out to demonstrate the utility of the subject invention. The following assays employ fluorescence for a determination of hIgG. To 100 μl of a solution of fluorescein-anti hIgG conjugate (4 F/hIgG), (8×10$^{-10}$ M) and anti(hIgG) (1.6×10$^{-8}$ M) in PBS, pH 7.8 containing 0.06% egg alumin and 0.05 NaN$_3$ was added 100 μl of hIgG in the above PBS buffer and the mixture incubated for 45 min. at room temperature. To the solution was then added 2.8 ml of buffer and 7 μl of antifluorescer, diluted 1:50 in the same buffer to provide a concentration of 0.18 mg/ml and the fluorescence read after 2 min. and then after a total of 45 min. The fluorimeter was a Perkin-Elmer MPF-2A, excitation 472 nm, emission scanned 510–525 nm. The following tables indicates the results:

Table I

| Sample No. | hIgG,M (in assay) | Fluorescence 45 min. | |
|---|---|---|---|
| 1 | 0 | 17.0, | 17.5 |
| 2 | 1 × 10$^{-6}$ | 20.0, | 20.5 |
| 3 | 1 × 10$^{-7}$ | 18.0, | 19.0 |
| 4 | 1 × 10$^{-8}$ | 20.0, | 21.0 |
| 5 | 1 × 10$^{-9}$ | 31.0, | 30.0 |
| 6 | 1 × 10$^{-10}$ | 27.0, | 27.0 |

The above procedure was repeated with the following exceptions: The buffer had 0.4 mg/ml of rabbit gamma globulin instead of egg albumin. The anti(hIgG) employed the fluorescein-anti hIgG conjugate at 1×10$^{-9}$ with a fluorescein-IgG ratio of 8.5 and the unlabelled anti(hIgG) was 4×10$^{-9}$ M. The antifluorescer was diluted 1 to 100. In reading, a B5 emission filter was employed. The following table indicates the results.

TABLE II

| Sample No. | hIgG,M (in assay) | Fluorescence 45 min. | |
|---|---|---|---|
| 1 | 0 | 14.5, | 17.5 |
| 2 | 1 × 10$^{-8}$ | 14.5, | 13.5 |
| 3 | 3 × 10$^{-9}$ | 16, | 16.5 |
| 4 | 1 × 10$^{-9}$ | 29, | 29 |
| 5 | 3 × 10$^{-10}$ | 27, | 28 |
| 6 | 1 × 10$^{-10}$ | 23.5, | 20.5 |

Viewing the 45 min. results, one obtains a biphasic curve which is sensitive to small changes in concentration in the range of about 10$^{-8}$ to 10$^{-10}$. Thus, by employing known standards, one can determine extremely small concentrations of hIgG in accordance with the above protocols. In substantially the same manner as described for the subject assays, one would be able to determine anti hIgG by performing the assay with a known amount of hIgG present and a known amount of the fluorescein-anti hIgG conjugate.

It is evident from the above results, that the subject assay provides an extremely sensitive technique for measuring low concentrations of analytes. Furthermore, a wide variety of different labels may be employed which have different advantages in different situations. Enzymes allow for amplification. Chemiluminescence is extremely sensitive, since individual events can be accurately counted. Stable free radicals allow for opaque solutions. Thus, the subject technique can be modified in accordance with the needs of a particular assay. A single medium may be used for the simultaneous determination of a number of different analytes.

Also of great importance is that the subject technique avoids the cumbersome and difficult isolations and purifications of antigens and antibodies. Because the modifier can suppress the signal of the label outside the complex, the background signal resulting from the presence of label attached to protein other than the desired antibody can be effectively suppressed.

Although the foregoing invention has been described in some detail by way of illustration and example for purposes of clarity of understanding, it will be obvious that certain changes and modifications may be practiced within the scope of the appended claims.

What is claimed is:

1. An assay method for determining a member of an immunological pair comprising a mono- or polyepitopic ligand and an anti(ligand) suspected of being present in a sample; said method employing:
   (1) labeled anti(ligand), wherein the label is capable of providing a detectable signal and said labeled anti(ligand) binds to said polyepitopic ligand to form a complex;
   (2) a macromolecular modifier which interacts with said label to modify the signal produced from said label and is inhibited from interacting with said label by said complex;
   (3) poly(ligand analog), wherein poly(ligand analog) has a plurality of epitopic sites capable of competing with said monoepitopic ligand for the binding sites of labeled anti(ligand), and capable of binding with anti(ligand) and labeled anti(ligand) to form a complex; and
   (4) polyepitopic ligand; with the proviso that poly(ligand analog) is only employed in an assay for monoepitopic ligand or anti(ligand) that binds monoepitopic ligand and polyepitopic ligand is only employed in an assay for anti(ligand) that binds polyepitopic ligand;

said method comprising;
   (A) combining in an assay medium for a time sufficient to form said complexes which sterically inhibit the approach of the macromolecular modifier to said label:
      (i) sample;
      (ii) labeled anti(ligand);
      (iii) modifier;
      (iv) poly(ligand analog) in an assay for monoepitopic ligand or anti(ligand) that binds monoepitopic ligand; and
      (v) polyepitopic ligand in an assay for anti(ligand) that binds polyepitopic ligand;
   (B) exposing said assay medium to an agent which interacts with said label to provide said detectable signal; and
   (C) measuring said detectable signal, wherein the measured detectable signal is directly related to the amount of said member in said medium.

2. A method according to claim 1, wherein said assay medium is at a pH in the range of about 5 to 10 and at a temperature during said measuring in the range of about 10° to 50° C.

3. A method according to claim 2, wherein said modifier is anti(label).

4. A method according to claim 3, wherein said label is a fluorescer.

5. A method according to claim 2, wherein said label is an enzyme.

6. A method according to claim 5, wherein said enzyme is an oxidoreductase.

7. A method according to claim 2, wherein said label is a member of a redox pair consisting of an oxidant and a reductant.

8. An assay method for determining a polyepitopic ligand suspected of being present in the sample; said method employing;
   (1) enzyme labeled anti(ligand), wherein the enzyme is capable of providing a detectable signal and said enzyme labeled anti(ligand) binds to said polyepitopic ligand to form a complex;
   (2) anti(enzyme), which binds to said enzyme to substantially inhibit said enzyme; said method comprising:
   (A) combining in an assay medium
      (i) sample;
      (ii) enzyme labeled anti(ligand);
   (B) incubating said assay medium for a time sufficient to form complexes which sterically inhibit the approach of said anti(enzyme) to said enzyme label;
   (C) adding to said assay medium anti(enzyme), substrates and any cofactors for said enzyme to produce a detectable signal as a result of the chemical change in the substrates or cofactors; and
   (D) measuring said detectable signal, wherein the measured detectable signal is proportional to the amount of said polyepitopic ligand in said assay medium.

9. A method according to claim 8, wherein said pH is in the range of about 6 to 9 and said temperature is in the range of about 15° to 40° C.

10. A method according to claim 9, wherein said enzyme is an oxidoreductase.

11. A method according to claim 10, wherein said oxidoreductase is a peroxidase and said substrates include hydrogen peroxide and a compound which forms a dye as a result of the enzymatic reaction.

12. A method according to claim 10, wherein said enzyme is glucose-6-phosphate dehydrogenase.

13. An assay method for determining a monoepitopic ligand suspected of being present in the sample;
   said method employing;
   (1) poly(ligand analog)
   (2) enzyme labeled anti(ligand), wherein the enzyme is capable of providing a detectable signal and said enzyme labeled anti(ligand) binds to said poly(ligand analog) to form a complex;
   (3) anti(enzyme), which binds to said enzyme to substantially inhibit said enzyme; said method comprising:
   (A) combining in an assay medium
      (i) sample;
      (ii) enzyme labeled anti(ligand);
      (iii) poly(ligand analog)
   (B) incubating said assay medium for a sufficient time to form complexes which sterically inhibit the approach of said anti(enzyme) to said enzyme label;
   (C) adding to said assay medium anti(enzyme), substrates and any cofactors for said enzyme to produce a detectable signal as a result of the chemical change in the substrates or cofactors; and
   (D) measuring said detectable signal, wherein the measured detectable signal is directly related to the amount of said monoepitopic ligand in said assay medium.

14. A method according to claim 13, wherein said pH is in the range of about 6 to 9 and said temperature is in the range of about 15° to 40° C.

15. A method according to claim 14, wherein said enzyme is an oxidoreductase.

16. A method according to claim 14, wherein said oxidoreductase is a peroxidase and said substrates include hydrogen peroxide and a compound which forms a dye as a result of the enzymatic reaction.

17. A method according to claim 14, wherein said enzyme is glucose-6-phosphate dehydrogenase.

18. A method according to claim 13, wherein said monoepitopic ligand is of a molecular weight in the range of about 125 to 1,000.

19. An assay method for determining a polyepitopic ligand suspected of being present in a sample; said method employing:
   (1) fluorescer labeled anti(ligand), wherein said fluorescer labeled anti(ligand) binds to said polyepitopic ligand to form a complex; and
   (2) anti(fluorescer); said method comprising:
   (A) combining in an assay medium at a pH of from about 6 to 9 and at a temperature in the range of about 15° to 40° C.
      (i) sample;
      (ii) fluorescer labeled anti(ligand);
   (B) incubating said assay medium for a sufficient time to form complexes which sterically inhibit the approach of said anti(fluorescer) to the fluorescent label;
   (C) adding anti(fluorescer) in an amount at least about stoichiometric with the amount of fluorescer and exciting fluorescer to an electronically excited state capable of emitting light; and
   (D) measuring said emitted light, wherein the measured emitted light is directly related to the amount of said polyepitopic ligand present in said medium.

20. A method according to claim 19, wherein said anti(fluorescer) is conjugated with quencher.

21. A method according to claim 19, wherein said polyepitopic ligand is γ-globulin.

22. An assay method for determining a monoepitopic ligand suspected of being present in a sample; said method employing:
   (1) poly(ligand analog), said poly(ligand analog) having a plurality of ligand analogs capable of competing with ligand for antiligand bonded to a water soluble hub nucleus
   (2) fluorescer labeled anti(ligand), wherein said fluorescer labeled anti(ligand) binds to said poly(ligand analog) ligand to form a complex;
   (3) anti(fluroescer); said method comprising:
   (A) combining in an assay medium at a pH of from about 6 to 9 and at a temperature in the range of about 15° to 40° C.
      (i) sample;
      (ii) fluorescer labeled anti(ligand);
      (iii) poly(ligand analog)
   (B) incubating said assay medium for a sufficient time to form complexes which sterically inhibit the approach of said anti(fluorescer) to the fluorescent label;
   (C) adding anti(fluorescer) in an amount at least about stoichiometric with the amount of fluorescer and exciting fluorescer to an electronically excited state capable of emitting light; and (D) measuring said emitted light, wherein the measured emitted light is directly related to the amount of said monoepitopic ligand present in said medium.

23. A method according to claim 22, wherein said anti(fluorescer) is conjugated with quencher.

24. An assay method for determining an anti(ligand) that binds to a polyepitopic ligand, said anti(ligand) suspected of being present in a sample, said method employing
(1) polyepitopic ligand;
(2) labeled anti(ligand), wherein the label is capable of providing a detectable signal and said labeled anti(ligand) and anti(ligand) bind to said ligand to form a complex;
(3) a macromolecular modifier which interacts with said label to modify the signal produced from said label and is inhibited from interacting with said label by said complex, said modifier being added in at least about an amount sufficient to interact with said label to modify said signal;
said method comprising:
(A) combining in an assay medium at a pH in the range of about 6 to 9 and at a temperature in the range of about 15° to 40° C. for a time sufficient to form complexes which sterically inhibit the approach of the macromolecular modified to said label
 (i) sample;
 (ii) labeled anti(ligand);
 (iii) modifier;
 (iv) polyepitopic ligand;
(B) exposing said assay medium to an agent which interacts with said label to provide said detectable signal; and
(C) measuring said detectable signal, wherein the measured detectable signal is directly related to the amount of said anti(ligand) in said medium.

25. A method according to claim 24, wherein said modifier is anti(label).

26. A method according to claim 25, wherein said label is an enzyme.

27. A method according to claim 25, wherein said label is a fluorescer and said modifier is antifluorescer in at least about stoichiometric amount based on the amount of said fluorescer in said assay medium.

28. An assay method for determining a member of an immunological pair comprising a mono- or polyepitopic ligand and an anti(ligand) suspected of being present in a sample;
said method employing:
(1) labeled anti(ligand), wherein the label is capable of providing a detectable signal and said labeled anti(ligand) binds to said polyepitopic ligand to form a complex;
(2) a Fab anti(label) which interacts with said label to modify the signal produced from said label and is inhibited from interacting with said label by said complex;
(3) poly(ligand analog), wherein poly(ligand analog) has a plurality of epitopic sites capable of competing with said monoepitopic ligand for the binding sites of labeled anti(ligand), and capable of binding with anti(ligand) and labeled anti(ligand) to form a complex; and
(4) polyepitopic ligand;
with the proviso that poly(ligand analog) is only employed in an assay for monoepitopic ligand or anti(ligand) that binds monoepitopic ligand and ligand is only employed in an assay for anti(ligand) that binds polyepitopic ligand;
said method comprising:
(A) combining in an assay medium for a time sufficient to form complexes which sterically inhibit the approach of the Fab anti(label) to said label:
 (i) sample;
 (ii) labeled anti(ligand);
 (iii) Fab anti(label);
 (iv) poly(ligand analog) in an assay for monoepitopic ligand or anti(ligand) that binds monoepitopic ligand; and
 (v) ligand in an assay for anti(ligand) that binds poly(epitopic ligand);
(B) exposing said assay medium to an agent which interacts with said label to provide said detectable signal; and
(C) measuring said detectable signal, wherein the measured detectable liquid is directly related to the amount of said member in said medium.

29. An assay composition for use in an assay method according to claim 1 which comprises the reagents labeled anti(ligand) and macromolecular modifier in relative amounts for substantially optimizing the response of the reagents in providing the detectable signal in relation to changes in the concentration of the member in said sample over the concentration range between $10^{-4}$ to $10^{-15}$ m.

30. An assay composition according to claim 29 wherein said modifier is anti(label).

31. An assay composition according to claim 29, including poly(ligand analog).

32. An assay composition according to claim 29, including polyepitopic ligand.

33. An assay composition for use in a method according to claim 9 which comprises the reagents enzyme labeled anti(ligand) and anti(enzyme) in relative amounts for substantially optimizing the response of the reagents in providing the detectable signal in relation to changes in the concentration of the member in said sample over the concentration range between $10^{-4}$ to $10^{-15}$ m.

34. An assay composition for use in a method according to claim 33, which comprises the reagents fluorescer labeled anti(ligand) and anti(fluorescer) in relative amounts for substantially optimizing the response of the reagents in providing the emitted light in relation to changes in the concentration of the ligand in said sample over the concentration range between $10^{-4}$ to $10^{-15}$ m.

35. An assay composition for use in a method according to claim 28 which comprises the combined reagents labeled anti(ligand) and Fab anti(label) in relative amounts for substantially optimizing the response of the reagents in providing the detectable signal in relation to changes in the concentration of the member in said sample over the concentration range between $10^{-4}$ to $10^{-15}$ m.

36. An assay composition according to claim 35, wherein said label is an enzyme.

37. An assay composition according to claim 35, wherein said label is a fluorescer.

* * * * *